United States Patent [19]

Turnbull

[11] Patent Number: 4,787,894
[45] Date of Patent: Nov. 29, 1988

[54] MECONIUM ASPIRATION DEVICE

[76] Inventor: Christopher J. Turnbull, 1134 Summit Ave., St. Paul, Minn. 55105

[21] Appl. No.: 112,550

[22] Filed: Oct. 26, 1987

[51] Int. Cl.$^4$ ............................................. A61M 25/00
[52] U.S. Cl. ....................................... 604/319; 604/73; 604/281; 128/207.14
[58] Field of Search ........................... 604/73, 319–321, 604/281; 128/207.14

[56] References Cited

U.S. PATENT DOCUMENTS

| | | | |
|---|---|---|---|
| 1,060,665 | 5/1913 | Bell | 604/281 |
| 1,931,720 | 10/1933 | Edgington | 128/350 |
| 3,169,528 | 2/1965 | Knox et al. | 604/281 |
| 3,674,404 | 7/1972 | Burlis et al. | 425/326 |
| 3,742,934 | 7/1973 | Holbrook et al. | 128/2 F |
| 3,776,222 | 12/1973 | Smiddy | 128/6 |
| 3,996,939 | 12/1976 | Sheridan et al. | 128/351 |
| 4,022,219 | 5/1977 | Basta | 128/351 |
| 4,133,656 | 1/1979 | Kippel et al. | 55/274 |
| 4,214,593 | 7/1980 | Imbruce et al. | 128/748 |
| 4,228,798 | 10/1980 | Deaton | 604/320 X |
| 4,275,724 | 6/1981 | Behrstock | 128/207.14 |
| 4,300,550 | 11/1981 | Gandi et al. | 128/207.18 |
| 4,320,756 | 3/1982 | Holmes | 128/206.12 |
| 4,372,336 | 2/1983 | Cornell et al. | 137/205 |
| 4,439,189 | 3/1984 | Sargeant et al. | 604/317 |
| 4,454,887 | 6/1984 | Krüger | 128/772 |
| 4,455,140 | 6/1984 | Joslin | 604/317 |
| 4,459,139 | 7/1984 | Von Reis et al. | 604/320 X |
| 4,465,483 | 8/1984 | Weilbacher | 604/317 |
| 4,510,931 | 4/1985 | Henderson et al. | 128/202.28 |
| 4,627,444 | 12/1986 | Brooker | 128/758 |
| 4,643,719 | 2/1987 | Garth et al. | 604/73 |
| 4,643,720 | 2/1987 | Lanciano | 604/95 |
| 4,650,476 | 3/1987 | Telang | 604/319 |
| 4,662,367 | 5/1987 | Gore, Jr. | 128/202.28 |

Primary Examiner—Dalton L. Truluck
Attorney, Agent, or Firm—Orrin M. Haugen; Thomas J. Nikolai; Frederick W. Niebuhr

[57] ABSTRACT

A device for aiding aspiration of meconium-stained fluids from infants at birth is disclosed. The device includes a unique endotracheal tube having a guide wire imbedded in its walls, a collection chamber in communication with said endotracheal tube, and a second tube having a bacterial/viral filter and a mouthpiece associated therewith which is used to evacuate the collection chamber and draw fluids through the endotracheal tube.

4 Claims, 1 Drawing Sheet

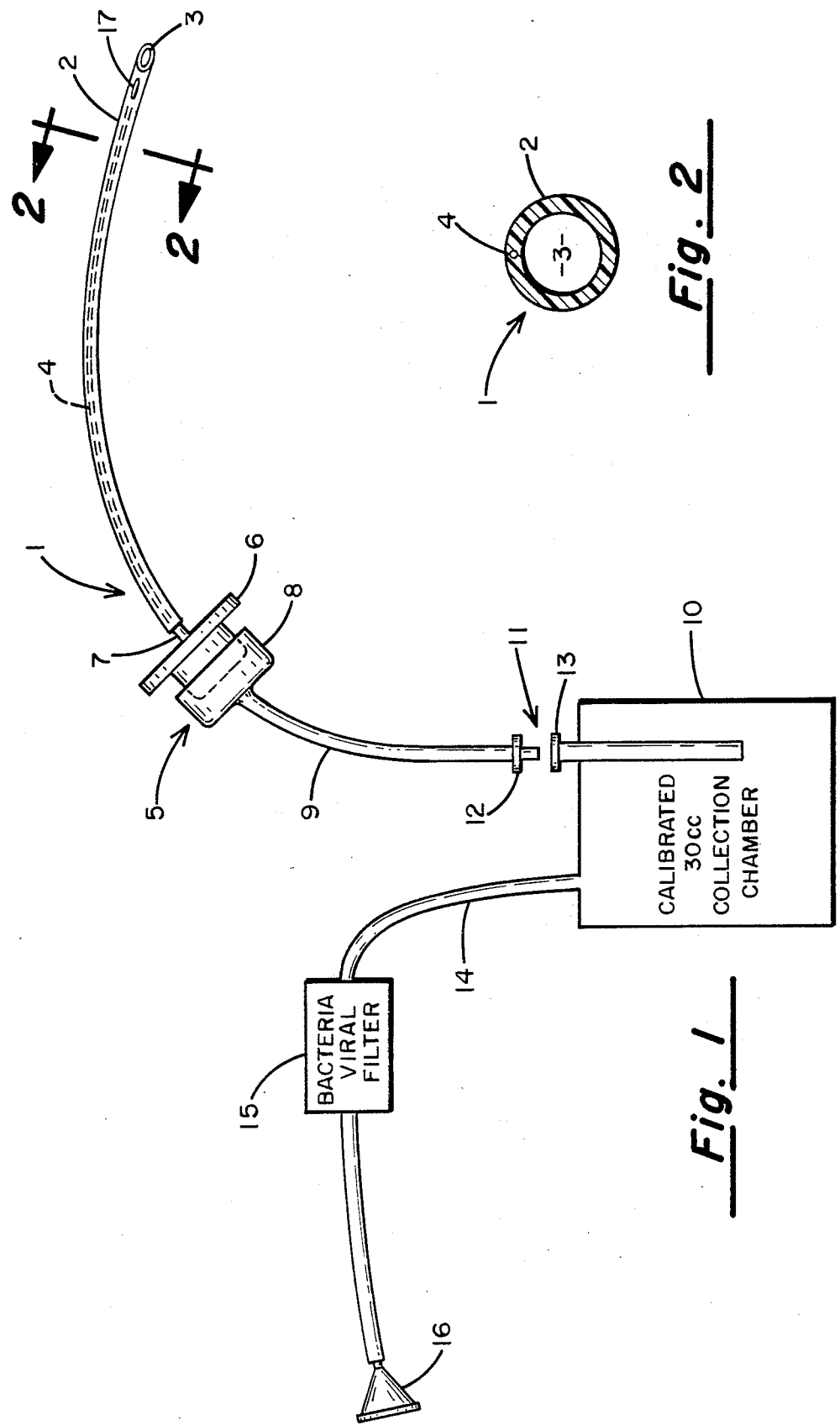

MECONIUM ASPIRATION DEVICE

BACKGROUND OF THE INVENTION

I. Field of the Invention

The present invention relates to a meconium respiration device and more particularly to a meconium aspiration device which includes an endotracheal tube having a guide or stiffening wire embedded within the wall of said tube, a calibrated collection chamber in communication with the endotracheal tube, a suction tube which leads to a mouthpiece, and a bacterial/viral filter contained within the suction tube.

II. Discussion of the Prior Art

Meconium aspiration syndrome in newborn infants is a potentially fatal condition, the risks of which can be reduced by aggressive airway management during and immediately after delivery.

Meconium-stained amniotic fluid is present in 9 percent to 14 percent of all pregnancies at the time of delivery. Increased postnatal morbidity and mortality rates have been associated with meconium-stained fluid. Meconium aspiration syndrome, which is initially manifested as respiratory distress, hypoxemia and acidosis and which may progress rapidly to respiratory failure, is of special concern.

This syndrome is generally thought to occur as a result of aspiration of meconium stained amnionic fluid with the first respirations after birth. It is believed that an effective means for reducing the risk of meconium aspiration syndrome is to evacuate the airway of the infant during and immediately after birth to remove any meconium-stained amniotic fluid that may have been inhaled by the infant.

In the prior art, various apparatus exists for evacuating meconium stained amnionic fluid from an infant's airway. However, these prior art devices are deficient in that they do not permit one to readily bend and form the endotracheal tube to be inserted in the airway so as to facilitate positioning of the distal port of such tube within the newborn's trachea. Similarly, those devices which are currently commercially available do not include a bacterial/viral filter that will protect the physician applying treatment as he applies oral suction to the device. Oral suction rather than connection to a vacuum pump is the preferred method because it permits the physician to carefully regulate the desired amount of suction to avoid damage to the infant's delicate throat and bronchial tissues and membranes. The need for such a bacterial/viral filter is becoming increasingly necessary, given the exponential rise in the number of cases involving mothers and infants who carry the AIDS virus. Hence, there is a real need for a meconium aspiration device which includes an easily formed endotracheal tube and an effective means for inhibiting bacteria and viruses from traveling through the oral suction tube to a point where they could infect the physician.

BRIEF DESCRIPTION OF THE INVENTION

The present invention is directed to a meconium aspiration device comprised of a flexible plastic endotracheal tube having a stiffening wire embedded in the wall thereof so as not to partially occlude the lumen thereof, a 30 cc calibrated collection chamber in communication with said endotracheal tube, a suction or evacuation line also in communication with the collection chamber, a mouthpiece associated with the suction tube, and a bacterial/viral filter in the suction tube between the collection chamber and the mouthpiece. The configuration of the present invention permits a physician to create a vacuum in the collection chamber by inhaling through the mouthpiece. This vacuum, in turn, will cause meconium stained fluids to be drawn from the infant's respiratory airway through the endotracheal tube. The bacterial/viral filter inhibits bacteria and viruses from traveling to the mouthpiece where they could infect the physician using the device.

OBJECTS

The principal object of the present invention is to provide an improved meconium evacuation apparatus having an endotracheal tube which can easily be bent to a desired shape.

Another object of the invention is to provide a meconium aspiration device through which suction can be applied orally by a physician.

Still another object of the invention is to provide an effective meconium aspiration device having a bacterial/viral filter for reducing the risk of bacterial or viral infections from being transmitted from the infant to the physician using the device.

These and other objects of the present invention will become more readily apparent from a reading of the following Description of the Preferred Embodiment in conjunction with the drawings.

BRIEF DESCRIPTION OF THE DRAWINGS

FIG. 1 is a plan view showing a meconium aspiration device of the present invention in assembled relation; and FIG. 2 is a greatly enlarged cross-sectional view through line 2—2 of FIG. 1 showing a cross-section of the endotracheal tube.

DESCRIPTION OF THE PREFERRED EMBODIMENT

As best shown in FIG. 1, the present invention is comprised of an endotracheal tube indicated generally by numeral 1 and having a cylindrical wall 2 which surrounds a lumen or passage 3. For use with newborn infants, the endotracheal tube 1 may be about 15 cm in length and have an outer diameter of 5 mm and an inner diameter of 3 mm. The proximal and distal ends of the cylindrical wall 2 comprising the tube 1 are open. The wall of the endotracheal tube is preferably made of a medical grade nontoxic, plastic such as polyvinyl chloride. The distal end of the tube 1 has a blunt and beveled tip. An important feature of the endotracheal tube 1 of the present invention which distinguishes it from other endotracheal tubes is the presence of a stiffening wire 4 which, as best shown in FIG. 2, is embedded in the plasticized polyvinyl chloride wall of the endotracheal tube during the extrusion process. The stiffening wire may extend from a point approximately ½ cm proximal of the Murphy eye 17 to a point approximately 11½ cm from the distal tip of the endotracheal tube. Given this orientation, the stiffening wire 4 permits the endotracheal tube to be bent and hold its shape as desired. At the same time, because it is not located on the outside of the tube, the stiffening wire does not interfere with or cause undue irritation of the infant's air passages during insertion or retraction. Further, because it is not contained in the passage or lumen 3 of the tube, it does not interfere with the flow of fluid material through the lumen.

As shown in FIG. 1, the endotracheal tube 1 has a standard sized endotracheal tube adapter device 5 attached to its proximal end. This adapter device 5 is comprised of a male member 6 having a tubular stub extending therefrom which is intended to be inserted in the proximal end of endotracheal tube 1. The adapter device also includes a female member 8 which is connected to a second length of polyvinyl chloride tubing 9 which typically may be 25 cm in length and a lumen 3.0 mm in diameter. The presence of adapter device 5 is deemed desirable because it allows the endotracheal tube to be used with other types of standard suction and aspiration devices as well as with a source of oxygen or air should it become necessary to ventilate the infant during the course of the meconium aspiration procedure.

To form a secure connection between the proximal end of the connecting tube 9 and the calibrated collection chamber 10, a twist-lock or a luer fitting 11 may be employed. This connector, which has a male end 12 associated with the connecting tubing 9 and a female member 13 associated with the collection chamber 10 provides an easy convenient means for removably attaching the endotracheal tube to the collection chamber. When assembled in this fashion, a first communicating passage is formed between the collection chamber and the "Murphy eye" opening 17 in the distal end portion of the endotracheal tube 1.

Also in fluid communication with the collection chamber 10 is a length of polyvinyl chloride tubing 14 which typically may be approximately 27 centimeters long. Disposed along this length of polyvinyl chloride tubing is a bacterial/viral filter 15 which is intended to preclude the transfer of bacteria or viruses beyond the filter, but still permits the suction of air from the end of the endotracheal tube, through the collection chamber 10 and through the filter 15. Finally, the apparatus of the present invention includes a mouthpiece 16. This mouthpiece is secured to the proximal end of tube 14.

When fully assembled as shown in FIG. 1, complete communicating passages created from the distal end of the endotracheal tube to the collection chamber and a second communicating passage is established between the collection chamber and the mouthpiece 16. Hence, by inhaling through suction piece 16, the physician can create a vacuum in the collection chamber 10 which will cause the aspiration of meconium tainted fluid and other mucous materials from the infant through the endotracheal tube into the graduated collection chamber. The chances of infection of the attending medical technician from the meconium or from other viruses or bacteria carried by the infant are greatly reduced due to the inclusion of the bacterial/viral filter 15 located in the suction tube 14.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. A meconium aspiration device comprised of:
   (a) an endotracheal tube having an elongated, flexible, plastic, generally annular wall surrounding a central lumen of a generally uniform diameter and extending the entire length thereof from a proximal end to a distal end through which meconium tainted fluid materials can be aspirated and a stiffening wire totally embedded in said wall without encroachment into the central lumen, said stiffening wire extending substantially the length of said tube from a location a predetermined distance distal of said proximal end to a location just short of said distal end;
   (b) a fluid collection chamber coupled to said endotracheal tube;
   (c) disconnectable adapter means interposed between said endotracheal tube and said collection chamber for allowing rapid exchange of a vacuum source used during aspiration with a source of breathable gas for allowing ventilation through said endotracheal tube; and
   (d) an evacuation tube also coupled in fluid communication with said collection chamber and having a bacterial/viral filter disposed within said evacuation tube.

2. The device as in claim 1 and further including a mouthpiece member associated with one end of said evacuation tube through which air can be drawn.

3. The device as in claim 1 wherein said endotracheal tube includes an opening of a predetermined size passing through said wall near the distal end thereof.

4. The device as in claim 3 wherein the wall of said endotracheal tube is formed with a blunt, beveled distal tip.

* * * * *